United States Patent [19]

Sollars, Jr.

[11] Patent Number: 4,702,597
[45] Date of Patent: Oct. 27, 1987

[54] PILE LAY MEASUREMENT SYSTEM
[75] Inventor: John A. Sollars, Jr., LaGrange, Ga.
[73] Assignee: Milliken Research Corporation, Spartanburg, S.C.
[21] Appl. No.: 846,212
[22] Filed: Mar. 31, 1986
[51] Int. Cl.[4] .................. G01B 11/26; G01N 21/59; G01N 21/89
[52] U.S. Cl. ........................... 356/138; 26/70; 250/572; 356/152; 356/238; 356/430
[58] Field of Search ............... 356/138, 238, 429, 430, 356/152; 26/70; 250/559, 562, 571, 572

[56] References Cited

U.S. PATENT DOCUMENTS 2,869,416  1/1959  Nieman et al. ............... 356/238
3,001,080  9/1961  Neil .
3,065,615  11/1962 Abrams ........................ 66/166
3,116,621  1/1964  Klein et al. ................... 66/166
3,435,240  3/1969  Brunton .
3,490,253  1/1970  Sick et al. .................... 66/166
3,556,665  1/1971  Hertel .......................... 356/238
4,248,533  2/1981  Shimada ....................... 356/238
4,338,032  7/1982  Bardsley et al. .............. 356/431
4,606,645  8/1986  Matthews et al. ............. 250/572

Primary Examiner—F. L. Evans
Attorney, Agent, or Firm—H. William Petry; Earle R. Marden

[57] ABSTRACT

Method and apparatus to measure the angle of pile lay to generate a signal which can be employed to automatically adjust another phase of the manufacturing operation to provide a desired pile effect on the fabric. Basically, the invention involves placing a light source on one side of the pile fabric and a light sensor on the other side of the fabric and varying the relative positions of the source and sensor to the pile on the fabric to obtain a measurement of optimum light transmittance.

5 Claims, 7 Drawing Figures

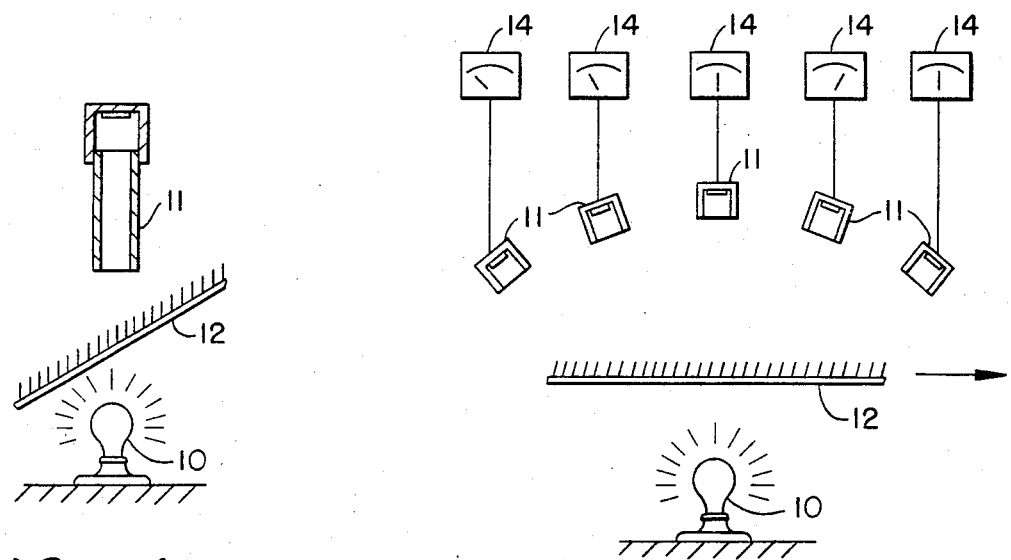
FIG. -1-
FIG. -2-
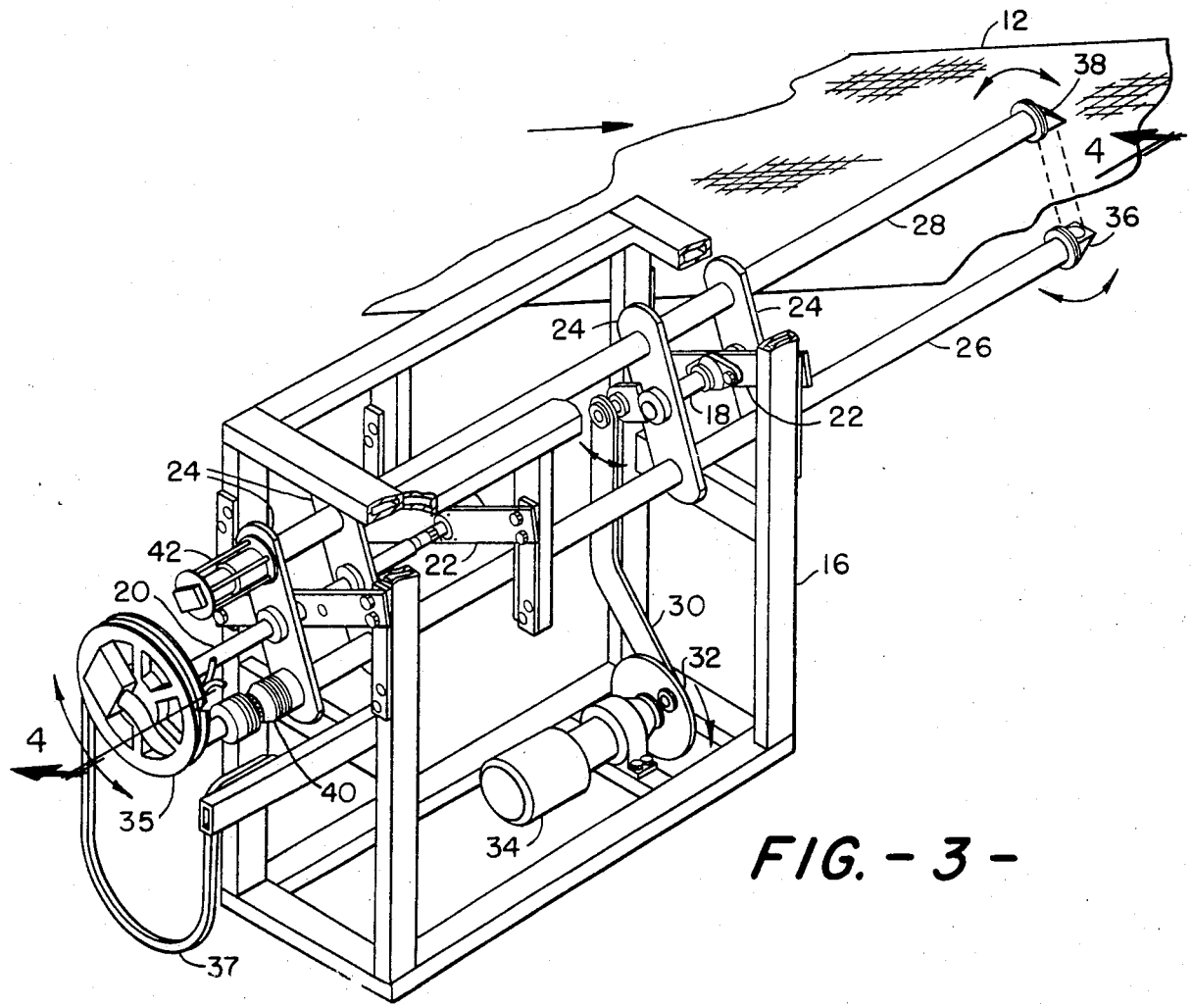
FIG. -3-

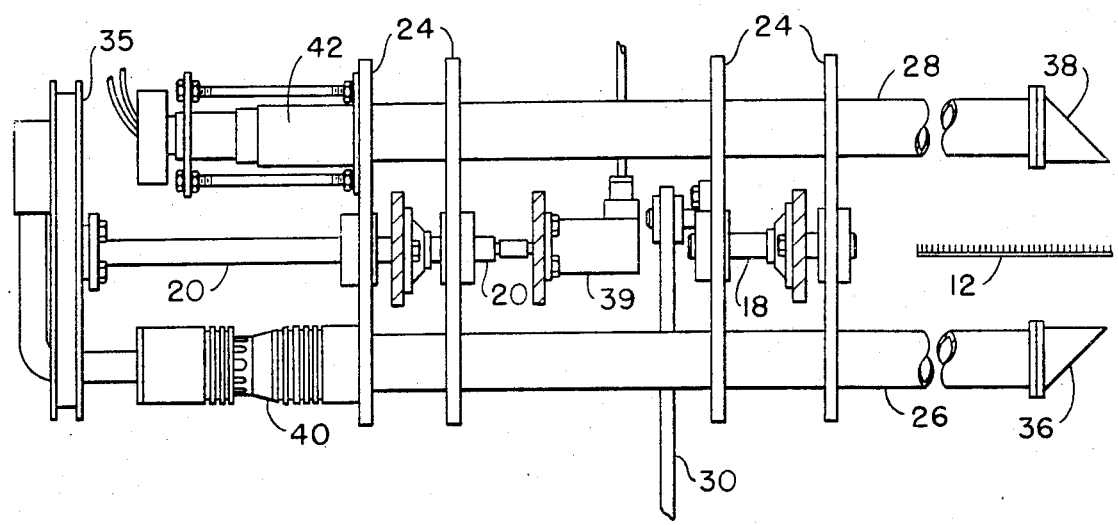
FIG. -4-
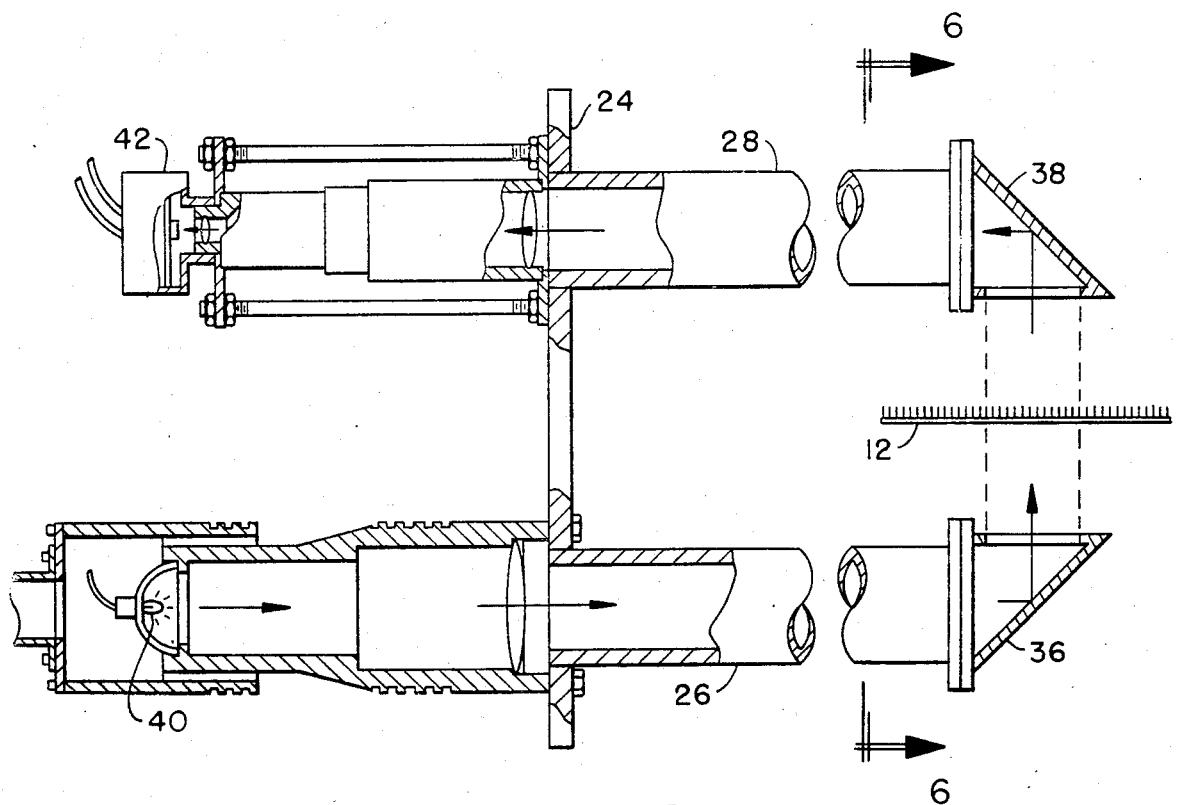
FIG. -5-

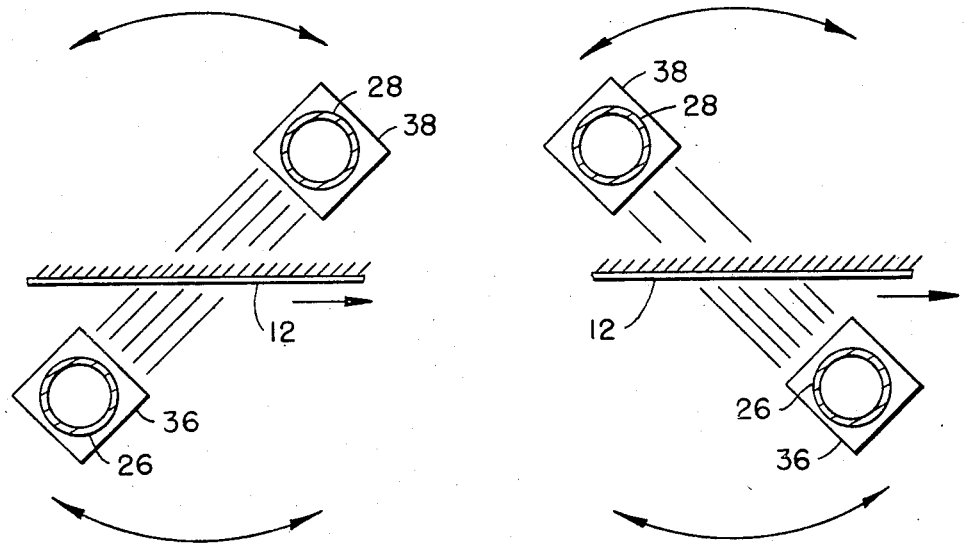
FIG. -6-
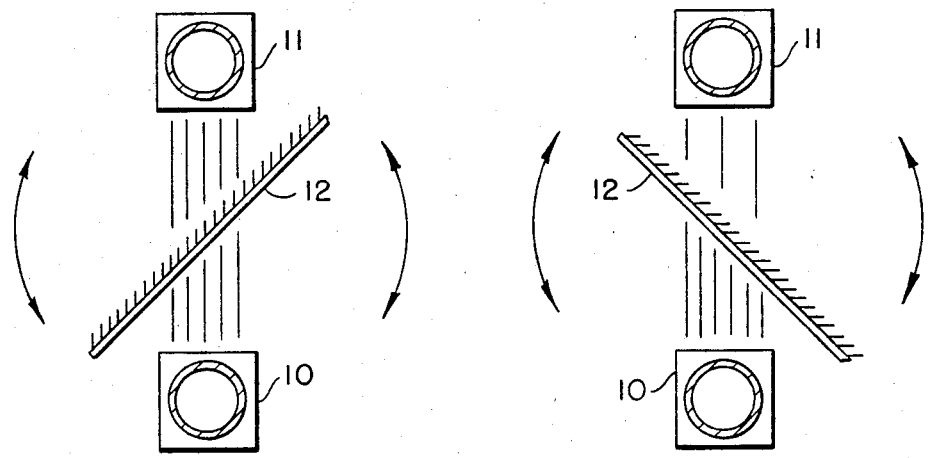
FIG. -7-

PILE LAY MEASUREMENT SYSTEM

This invention relates to a system to measure the pile angle of the upstanding fibers in a pile fabric to generate a signal which can be employed to provide a pile fabric with the desired pile angle.

As is well known in the industry, the angle of pile lay in a velvet or pile fabric affects many characteristics of the fabric such as softness, appearance, the overall aesthetic worth of the fabric and the customer's perception of shade and/or color. Prior to this invention, the angle of the pile has been determined by visual analysis which is dependent upon the perception of the viewer and does not reflect the overall standard for a desired style of pile fabric.

Therefore, it is an object of the invention to provide a system to automatically measure the pile angle of the fibers in a velvet or pile fabric.

Other objects and advantages of the invention will become readily apparent as the specification proceeds to describe the invention, with reference to the accompanying drawing, in which:

FIGS. 1 and 7 are schematic representations of the basic concept of the invention;

FIG. 2 is a second schematic representation of the inventive concept;

FIG. 3 is a perspective view of the preferred apparatus to employ the invention;

FIG. 4 is a view taken on line 4—4 of FIG. 3;

FIG. 5 is a blown-up cross-section view of the apparatus of FIG. 4, and

FIG. 6 is a schematic view taken on line 6—6 of FIG. 5.

The basic concept of the invention is directed to passing light through a pile fabric and plotting a curve of relative light transmittance versus the angle of the light beam to determine the pile angle. The plotted curve is influenced by the two factors of pile angle and nature of the base construction of the pile construction. Since the base construction of the pile fabric is a known factor, the graph plotted by the light transmittance recorded provides the desired information as to pile angle. In its simplest form, the measured light transmittance signals can be used to plot a graph but, in a manufacturing environment, it is desired that the measured signal be compared to a standard to make a process adjustment when the signal varies from the desired standard.

As mentioned before, it is desired to generate a signal which measures light transmittance through a pile fabric at various angles. This can be accomplished as shown in FIG. 1 by having a fixed light source 10, a fixed light sensor 11, and an oscillating pile fabric 12.

In a manufacturing operation, it is desired to scan a moving fabric, which is normally in a horizontal plane, and move either the light source or the light sensor to determine the angle of pile lay. FIG. 2 represents a system in which the pile fabric 12 moves horizontally above a light source 10 and the sensor 11 is rotated or moved from one angular position to another to measure the light transmittance through the fabric 12. The angular position of the sensor 11 is known and the reading on the indicator 14 can be visually observed or automatically transmitted to a recording device for process control.

FIGS. 3-6 illustrate the preferred form of the invention wherein the fabric 12 passes horizontally between the light source and the light sensor and the light source is rotated relative to the fabric 11 to vary the angle of the light beam.

The apparatus of FIGS. 3-6 is oscillated in a frame 16 on shafts 18 and 20 supported in a support member 22 connected to the frame 16. Each of the shafts 18 and 20 are fixed to a two support members 24 through which the tubes 26 and 28 project. The tubes 26 and 28 are oscillated by a crank arm 30 connected at one end to one of the support members 24 and at the other end to an eccentric 32 driven by the motor 34. Mounted on one end of shaft 20 is a pulley 35 which rotates with the shaft 20 to act as an accumulator for the cables 37 which supply power and electrical connection to the various components of the system. Mounted on the end of the shaft 20 is the angle position sensor 39 which provides real time information as to the angle of the light beam.

The tubes 26 and 28, in conjunction with the prisms 36 and 38 at the end thereof, form a folded light beam apparatus to scan the fabric 12. The light from the light source 40 travels down through the tube 26 and is transmitted through the fabric 12 by the prism 36 to the prism 38. The prism 38 deflects the transmitted light beam back down the tube 28 to the light sensor 42 which send a suitable signal to a collection apparatus such as a computer. The light source and light sensor can be suitable commercially available devices such as a photo-cell and photo-sensitive eye but other devices can be used within the scope of the invention.

It can be seen that the above described apparatus oscillates the light source relative to the fabric 12 to provide a continuous readout of the pile angle so it can be plotted by a suitable device receiving signals from the sensor 42. This plot can be used as a visible indication of the pile lay or can be automatically employed to control a component in the fabric treatment process to obtain a desired pile angle on the fabric 12. An example of such use would be to use the apparatus in line with a brushing and heat setting operation and feed back the signal obtained to automatically control the brushing and/or heat setting of the scanned pile fabric.

Although the preferred embodiments of the invention have been described, it is contemplated that many changes may be made without departing from the scope or spirit of the invention and it is desired that the invention be limited only by the scope of the claims.

I claim:

1. A method of measuring the pile angle of the fibers in a pile fabric comprising the steps of: supplying a pile fabric, placing a light source on one side of the pile fabric, placing a light sensor on the other side of the pile fabric, varying the transmittance of light from the light source to the light sensor in its passage through the pile fibers on the pile fabric by varying the angular position of the pile fabric, the angular position of the light source or the angular position of the light sensor and measuring the light transmittance from the light source through the pile fabric as the light transmittance is varied.

2. The method of claim 1 wherein the light source is moved relative to the light sensor.

3. The method of claim 1 wherein the light sensor is moved relative to the light source.

4. The method of claim 1 wherein the pile fabric is oscillated between the light source and light sensor.

5. Apparatus to measure the angle of pile fibers on the surface of a moving pile fabric comprising: a frame, a pair of tubes spaced from another and rotably supported in said frame, said tubes being supported generally parallel to one another with each having a prism in the same corresponding end thereof, a light source in the other end of one of said tubes, a light sensor in the corresponding end of the other of said tubes, means to supply a pile fabric between said prisms and means operably associated with said tubes to oscillate said tubes relative to the pile fabric between said prisms.

* * * * *